United States Patent
Lo et al.

(10) Patent No.: US 10,949,966 B2
(45) Date of Patent: Mar. 16, 2021

(54) DETECTING AND CLASSIFYING MEDICAL IMAGES BASED ON CONTINUOUSLY-LEARNING WHOLE BODY LANDMARKS DETECTIONS

(71) Applicant: Siemens Healthcare GmbH, Erlangen (DE)

(72) Inventors: Ren-Yi Lo, Plainsboro, NJ (US); Arnaud Gaillard-Moguilny, Lawrenceville, NJ (US); Sasa Grbic, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 304 days.

(21) Appl. No.: 16/019,579

(22) Filed: Jun. 27, 2018

(65) Prior Publication Data
US 2019/0057501 A1    Feb. 21, 2019

Related U.S. Application Data (60) Provisional application No. 62/547,372, filed on Aug. 18, 2017.

(51) Int. Cl.
| | |
|---|---|
| *G06T 7/00* | (2017.01) |
| *G06K 9/62* | (2006.01) |
| *G06T 7/11* | (2017.01) |
| *G16H 30/40* | (2018.01) |
| *G06N 20/00* | (2019.01) |
| *A61B 5/055* | (2006.01) |

(Continued)

(52) U.S. Cl.
CPC .......... *G06T 7/0012* (2013.01); *A61B 5/055* (2013.01); *G06K 9/626* (2013.01); *G06K 9/6267* (2013.01); *G06N 20/00* (2019.01); *G06T 7/11* (2017.01); *G16H 30/40* (2018.01); *A61B 5/7264* (2013.01); *A61B 8/4416* (2013.01); *G06K 9/6229* (2013.01); *G06K 2209/05* (2013.01)

(58) Field of Classification Search
None
See application file for complete search history.

(56) References Cited

U.S. PATENT DOCUMENTS

| 9,569,736 | B1 * | 2/2017 | Ghesu | G06K 9/6267 |
| 9,697,598 | B2 * | 7/2017 | Serlie | G06T 11/60 |
| 9,779,505 | B2 * | 10/2017 | Koktava | G06T 7/0012 |

(Continued)

OTHER PUBLICATIONS

Extended European Search Report (EESR) dated Jan. 14, 2019 in corresponding European Patent Application No. 18186362.2.

*Primary Examiner* — Anand P Bhatnagar (57) ABSTRACT

A computer-implemented method for automatically generating metadata tags for a medical image includes receiving a medical image and automatically identifying a set of body landmarks in the medical image using one or more machine learning models. A set of rules are applied to the set of body landmarks to identify anatomical objects present in the image. As an alternative to using the set of rules, in some embodiments, one or more machine learning models to the set of body landmarks to identify anatomical objects present in the image. Once the anatomical objects are identified, metadata tags corresponding to the anatomical objects are generated and stored in the medical image. Then, the medical image with the metadata tags is transferred to a data repository.

20 Claims, 5 Drawing Sheets

(51) Int. Cl.
*A61B 5/00* (2006.01)
*A61B 8/00* (2006.01)

(56) References Cited

U.S. PATENT DOCUMENTS

| | | | |
|---|---|---|---|
| 10,037,603 B2* | 7/2018 | Lay | G06K 9/4642 |
| 10,360,999 B2* | 7/2019 | Bernard | A61B 6/5288 |
| 10,489,907 B2* | 11/2019 | Rowley Grant | G06T 11/008 |
| 2015/0302580 A1* | 10/2015 | Serlie | G06T 7/11 |
| | | | 382/131 |
| 2016/0063720 A1* | 3/2016 | Han | G06T 7/10 |
| | | | 382/131 |
| 2016/0092748 A1* | 3/2016 | Koktava | G06T 7/0012 |
| | | | 382/128 |
| 2016/0328855 A1 | 11/2016 | Lay et al. | |
| 2017/0057169 A1* | 3/2017 | Grbic | B29C 64/386 |
| 2017/0358075 A1* | 12/2017 | Cao | G06T 7/11 |
| 2018/0129900 A1* | 5/2018 | Kiraly | G16H 30/20 |
| 2018/0256042 A1* | 9/2018 | Beckers | A61B 5/026 |

\* cited by examiner

DETECTING AND CLASSIFYING MEDICAL IMAGES BASED ON CONTINUOUSLY-LEARNING WHOLE BODY LANDMARKS DETECTIONS

CROSS-REFERENCE TO RELATED APPLICATIONS

This application claims the benefit of U.S. Provisional Application Ser. No. 62/547,372 filed Aug. 18, 2017, which is incorporated herein by reference in its entirety.

FIELD OF THE INVENTION

The invention relates generally to the detection and classification of medical images based on continuously-learning whole body landmarks detection. The techniques described herein may be applied, for example, as a post-processing step during image acquisition to provide human-readable information (referred to herein as "tags") that specify body parts and organs present in an image.

BACKGROUND

In the healthcare domain, researchers, scientist and other professionals work with medical images acquired through various image modalities. Finding specific cases or images from a large archive is often tedious, manual work, because not enough information is stored with the medical images. In addition, these medical images often follow an industry-standard format, such as DICOM images, while others may follow other standards (e.g., Neuroimaging Informatics Technology Initiative or "NIfTI") or be a more generic export (e.g., jpg, png, etc.). Depending on the format, these medical images may or may not have metadata information associated with the image, including tags describing the body part examined, organ of interest, acquisition protocol, or study description. Many image formats do not allow the specification of metadata tags or other metadata information (e.g., NIfTI, jpg). Even in formats where metadata can be used, the values are often missing or the information is incorrect. Correct and descriptive metadata often depends on the department's acquisition process at scan time, and often does not have a standardized approach across departments or institutions.

Conventional solutions only approach this problem through the meta data information via a rules-based approach. This current approach is limited to DICOM formatted images; it also assumes that the metadata information is readily available, and that it is error-free. The solution approach looks at the metadata tag 'StudyDescription'. This tag is filled with free-text describing how the study has been performed. From this free-text the solution deduces what anatomical object was studied and can be extracted. This solution has been proven to be somewhat effective at 99.94%, but does not consider the case when the metadata is not available (as is the case in other medical imaging formats), is left blank, or is incorrectly filled out. Additionally, in some instances, there is also the issue that the description filled out in the Study Description does not follow a rigorous guideline and is not harmonized (e.g., using the keyword "Lung" or "Chest").

The present disclosure is directed to overcoming these and other problems of the prior art.

SUMMARY

Embodiments of the present invention address and overcome one or more of the above shortcomings and drawbacks, by providing methods, systems, and apparatuses related to the detection and classification of medical images based on continuously-learning whole body landmarks detection. More generally, the techniques described herein address how to accurately obtain body part and organ information of the medical image without relying or deducing information from the metadata. More specifically, rather than parsing metadata, the techniques described herein derive information from the image itself.

According to some embodiments, a computer-implemented method for automatically generating metadata tags for a medical image includes receiving a medical image and automatically identifying a set of body landmarks in the medical image using one or more machine learning models. A set of rules are applied to the set of body landmarks to identify anatomical objects present in the image. As an alternative to using the set of rules, in some embodiments, one or more machine learning models are applied to the set of body landmarks to identify anatomical objects present in the image. Once the anatomical objects are identified, metadata tags corresponding to the anatomical objects are generated and stored in the medical image. Then, the medical image with the metadata tags is transferred to a data repository.

According to other embodiments, a system for automatically generating metadata tags for a medical image includes a medical image scanner and an image processing system comprising one or more processors. The medical image scanner is configured to acquire a medical image. The processors in the image processing system are configured to automatically identify a set of body landmarks in the medical image. Based on those landmarks, the processors identify anatomical objects present in the image and generate one or more metadata tags corresponding to the anatomical objects. The processors then store the metadata tags in the medical image and transfer the medical image with the metadata tags to a data repository.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

For example.

DETAILED DESCRIPTION

Systems, methods, and apparatuses are described herein which relate generally to the detection and classification of medical images based on landmarks detected in the images. Briefly, the techniques described herein may be understood as entailing two distinct steps. First, a landmarking engine is applied to a medical image to identify a set of landmarks present in the image. Then, using these landmarks, metadata tags are identified that describe body parts and/or organs present in the image. As described in further detail below, the identification of metadata tags can be performed using a rules-based or machine learning-based approach. The techniques described herein aid in the automation of metadata tag generation. Also, where metadata tags are already present in an image, the disclosed techniques may be used to correct any incorrect tags and ensure consistency across an image archive or other repository.

Figure 1A:
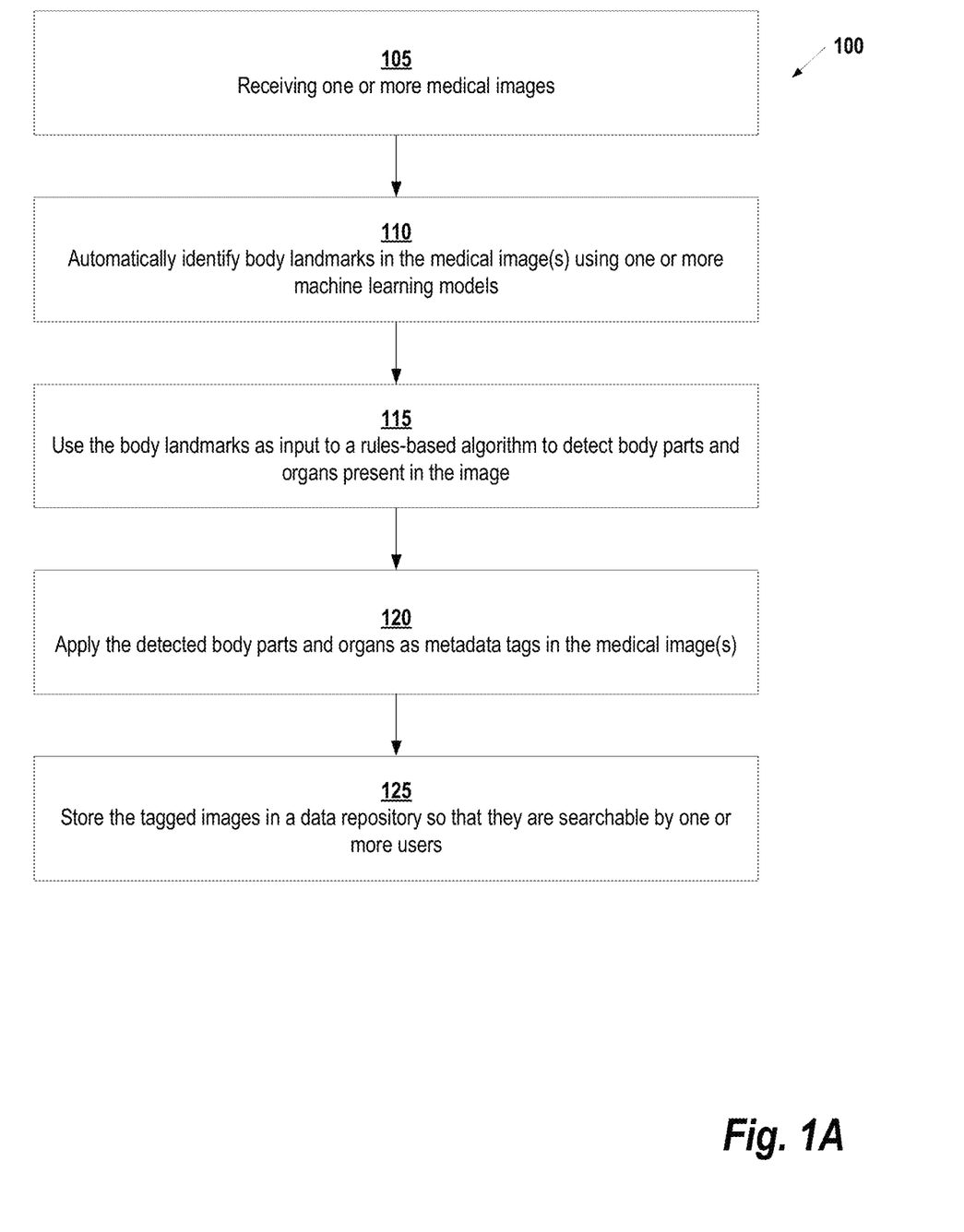
FIG. 1A illustrates a method for detecting and classifying medical images based on landmarks detected in the images.

FIG. 1A illustrates a method 100 for detecting and classifying medical images based on landmarks detected in the images. Starting at step 105, an image processing system receives one or more medical images. The term "image processing system," as used herein refers to a computer system with resource capable of processing images in an optimal manner. One example architecture is shown below with reference to FIG. 4. It should be noted that this architecture is merely exemplary and, in other embodiments, different architectures can be used. For example, in some embodiments, multiple compute nodes are a used in a cluster or a cloud infrastructure such as Amazon Web Services (AWS). The term "receives" should be broadly understood to include any technique for the image processing system acquiring the medical images. Thus, in some embodiments, the medical images may be sent to the image processing system as an input. In other embodiments, the image processing system collects the medical images from a database or other storage medium when a software application corresponding to the method 100 is executed. In some embodiments, the image processing system is included in the image scanner that acquires the medical images. For example, in one embodiment, the image processing system is executed by a computer within a magnetic resonance image (MRI) system. After the MRI data is acquired and reconstructed, the method 100 is automatically executed using the reconstructed images as input.

At step 110 the image processing system automatically identifies landmarks in the medical image by executing one or more machine learning models with the images as input. These landmarks may correspond to body parts (e.g., abdomen), organs (e.g., liver), or other anatomical objects (e.g., veins or nerves). In some embodiments, landmarks for abnormalities (e.g., lesions) may also be identified. Each machine learning model is trained based on labeled training images to identify landmarks at various anatomical views. The output of these machine learning models is a set of body landmarks that it recognizes in the image volume, such as 'Liver Top', 'Carina Bifurcation' or 'Right Knee'. One example machine learning algorithm for navigation of image parsing with deep reinforcement learning is described in U.S. Pat. No. 9,569,736 entitled "Intelligent medical image landmark detection," the entirety of which is incorporated herein by reference.

Next, at step 115, using the set of landmarks (i.e., name of the landmark and position), a rules engine is executed to detect which body part(s) and organ(s) are present in the medical image. The term "rules engine" is used herein to refer to any executable application or other software that executes rules. Each rule checks for the occurrence of conditions and, if the condition is met, one or more actions are performed.

At their most basic level, the rules used herein may be understood as listing one or more body parts or organs for a group of landmarks linked by one or more conditions. For example, a rule may indicate that the inclusion of two particular landmarks indicates that one or more organs are present the input image. More complex rules may be possible as well. For example, one rule may indicate that the presence of certain landmarks and the absence of other landmarks correspond to body parts or organs. Additionally, rules can be executed in sequence to provide more complex tags. For example, after executing a first rule to determine a first body part, a second rule can be executed that uses both the landmarks and the first body part to determine a second body part. In this way, sub-sections of anatomy can be identified. For example, the first body part may specify the presence of the heart in the image and the second body part may indicate specify chambers, arteries, etc.

Figure 1B:
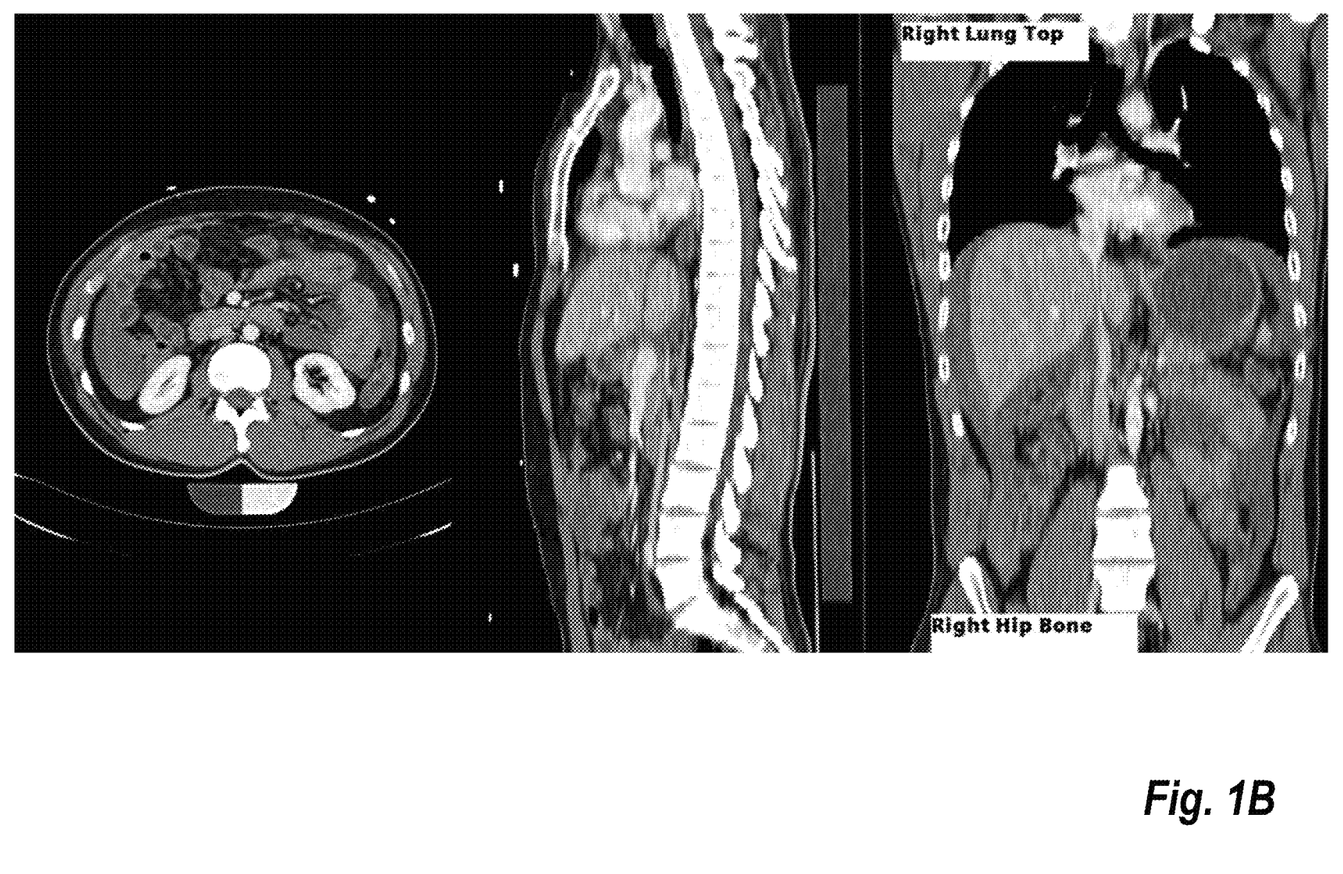
FIG. 1B shows example medical image where the upper bound landmark is labeled as "Right Lung Top" and the lower bound landmark is labeled as "Right Hip Bone;"

Continuing with reference to FIG. 1A, at step 120, the list of various body parts and organs are then stored as metadata tags in the medical images. For example, if the processing performed at step 115, indicates the presence of the right knee, the metadata tag Right Knee' may be generated. The correspondence between anatomical objects and the metadata tags may be established, for example, using a dictionary lookup system. That is, given an anatomical object, the algorithm returns the particular tag. In some embodiments, to detect the body part(s) and organ(s) in the medical image, every anatomical object has a defined upper bound and a lower bound. As an input to the dictionary lookup system, the uppermost (or "upper bound") landmark and the lowermost (or "lower bound") landmark may be used. For example, FIG. 1B show an example of medical images where the upper bound landmark is labeled as "Right Lung Top" and the lower bound landmark is labeled as "Right Hip Bone." To output the result, the dictionary lookup system looks which organs and body parts have both their bounds between the uppermost and lowermost landmark of the image. In some embodiments, each anatomical object also has a defined left bound and a right bound between which the object must be located. The terms "left" and "right" in this context are with reference to the coordinate system that defines the upper and lower bounds.

The descriptors output by the landmarking algorithm (e.g., "Right Lung Top") can be used directly as the tags in the metadata. Alternatively, in some embodiments, the dictionary lookup algorithm may be robust enough to provide different tags for a particular anatomical object based on one or more input parameters. For example, one medical institution may use the tag "Upper Liver" to refer to the upper portion of the liver, while another medical institution may use the tag "Liver Top." The medical institution or another identifier could be provided as an input to the dictionary lookup system to allow it to select the appropriate tag for a particular institution.

Once all of the metadata tags have been established, they are stored in correspondence with the medical image at step 125. For example, if the format of the image supports embedded metadata, the tags may be stored directly in the image itself. If embedded metadata is not supported, the tags may be saved in a separate file with a reference to the image. Alternatively, in some embodiments, a data model (e.g., json) is developed to define a custom meta model for body part/organ/type and reference to the image itself. This meta information can then be indexed for an easy, unstructured search. Finally, at step 125, the image with its metadata is stored in an archive or other data repository for later access and analysis. Once stored, the images are searchable by one or more users via their metadata tags.

In some instances, the image used as input may already comprise DICOM tags or other metadata with anatomical objects. In some embodiments, the method 100 may be configured to ignore this metadata and only consider as input the landmarks and their position. In this way, the method 100 solves the problem where medical images do not contain metadata information (i.e., NIfTI) or the DICOM header (meta data) is empty or inaccurate.

Figure 2:
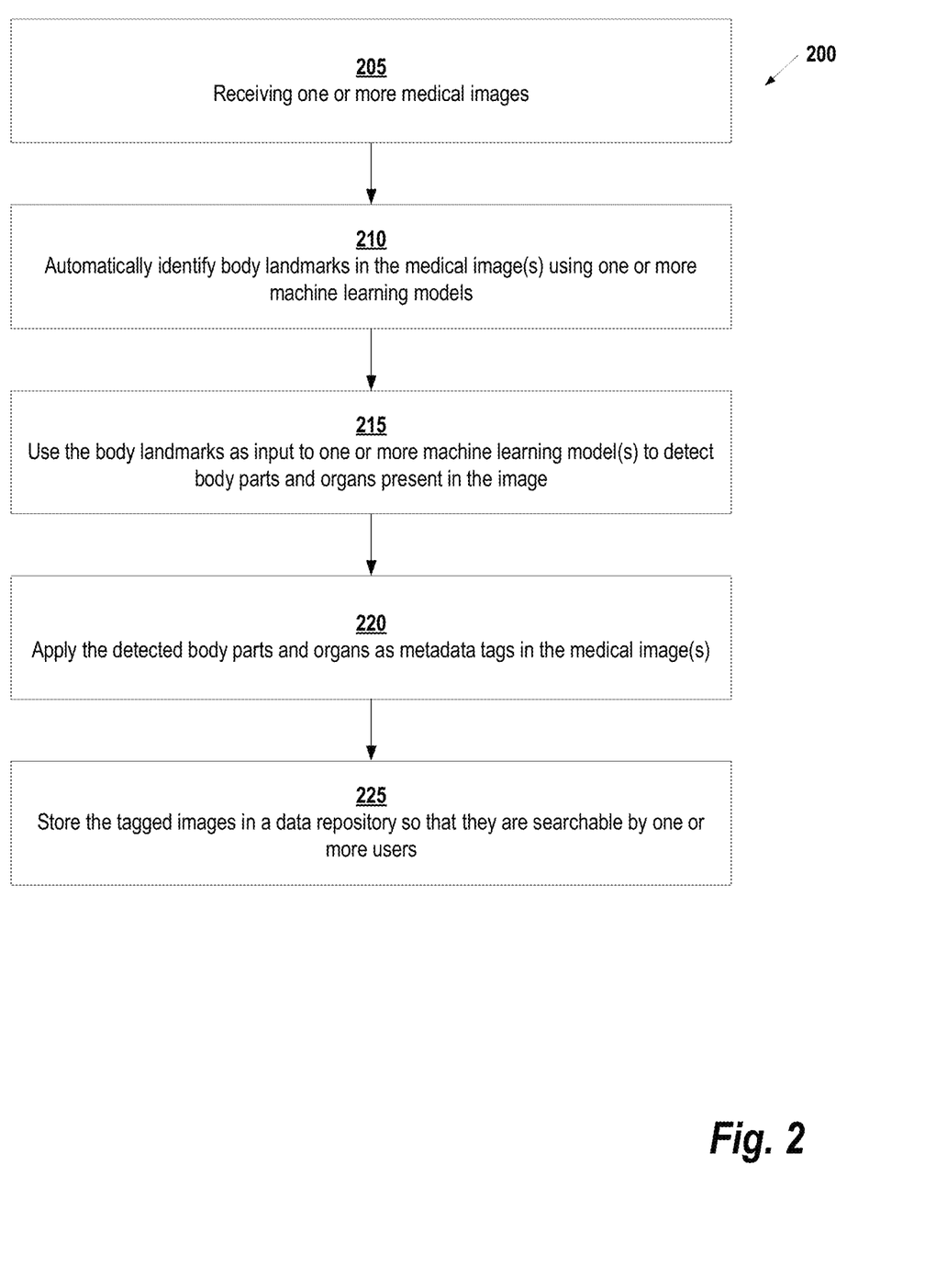
FIG. 2 illustrates an alternative method for detecting and classifying medical images based on landmarks detected in the images.

FIG. 2 illustrates an alternative method 200 for detecting and classifying medical images based on landmarks detected in the images. In this example, the rule-based approach is replaced by a machine-learning approach, allowing the rules for body part and organ definition to be fine-tuned via a machine learning based method. Here steps 205 and 210 may be implemented in the same manner as discussed above with reference to steps 105 and 110 of the method 100 of FIG. 1A. However, at step 215, instead of the rules-based approach, a machine learning model is used to identify metadata tags based on landmarks. Using such a machine-learning approach, the rules for body part and organ definition can be fine-tuned via a machine learning. Examples of machine learning models that may be applied at step 215 include support vector machines (SVMs), decision trees or random forests, standard neural networks, and convolutional neural networks.

Various techniques may be used for training the machine learning model used at step 215. In general, training is performed by providing a set of images with labeled landmarks and corresponding body parts. This training set is preferably large and diverse enough such that the trained model can support a wide range of anatomies and views. Various techniques may be used for labeling the data. For example, in some embodiments, the machine learning model is trained using medical images labeled with an upper bound landmark, a lower bound landmark, and one or more labeled anatomical objects located between the upper bound landmark and the lower bound landmark. The medical images may be further labeled with a left bound landmark and a right bound landmark, and the one or more labeled anatomical objects are located between the left bound landmark and the right bound landmark. The details of the training will depend on the type and characteristics of the model being used. For example, in a random forest implementation, a plurality of decision trees is generated with each decision tree comprising a randomly selected subset of the landmarks. To generate a tree, a subset is split into daughter nodes by considering the landmarks in the training data. During deployment, as new landmarks are received, the rules of each randomly generated decision tree are used to predict an anatomical object. The votes of each predicted anatomical object are calculated and the highest voted object is considered the most like object corresponding to the input landmarks.

Continuing with reference to FIG. 2, at step 220, the list of various body parts and organs output by the machine learning model is applied as metadata information to the medical images. Once all of the metadata tags have been established, they are stored in a data repository in correspondence with the medical image at step 225. Once in the data repository, the images are searchable via their metadata tags. The details of implementing steps 220 and 225 are similar to those discussed above with regards to steps 120 and 125 of FIG. 1A.

Figure 3:
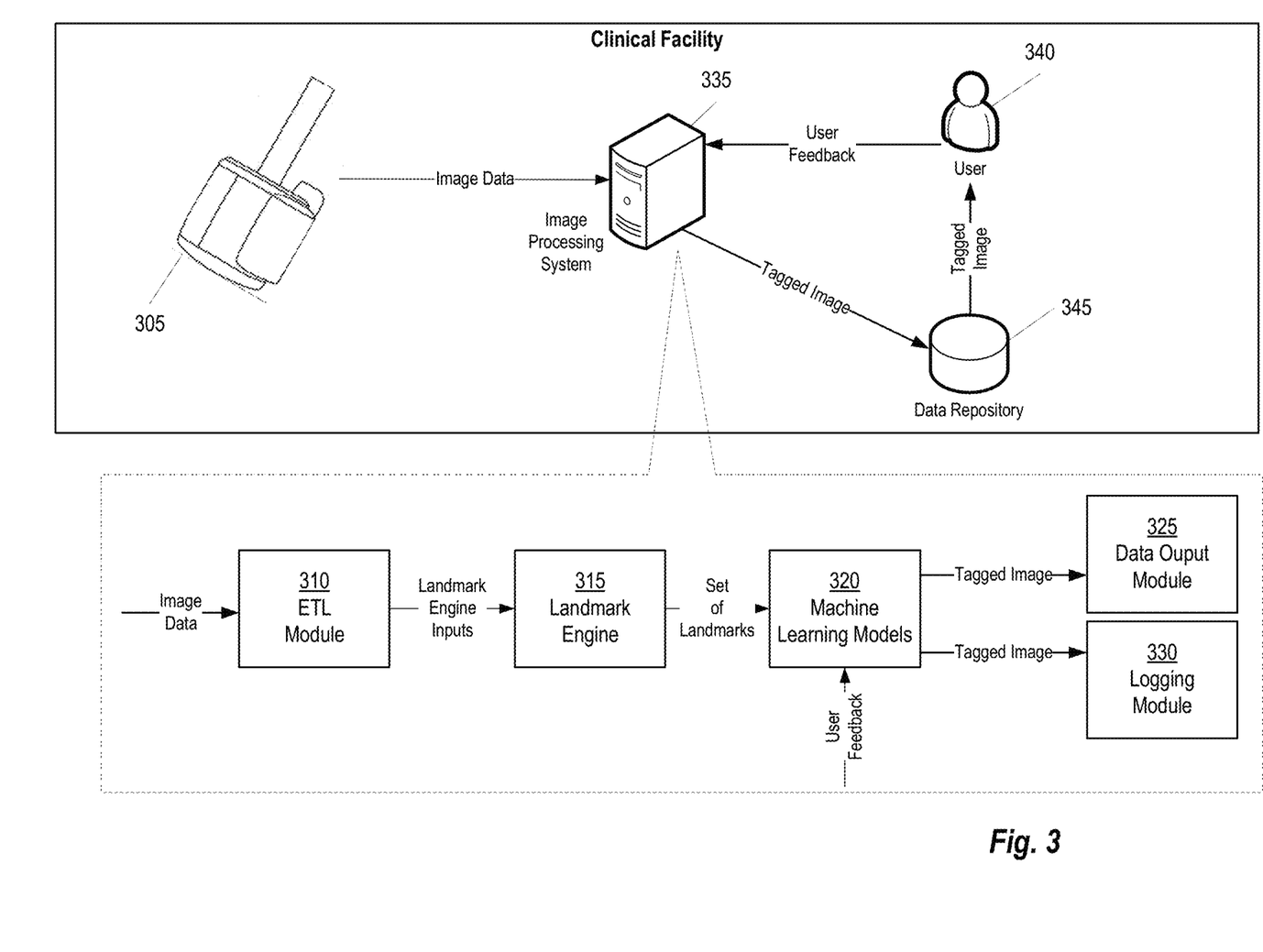
FIG. 3 illustrates a system that could be used to implement the method illustrated in FIG. 2.

FIG. 3 illustrates a system that could be used to implement the method 200 illustrated in FIG. 2. In this example, a magnetic resonance imaging (MRI) scanner 305 sends image data to an image processing system 335. Within the image processing system 335, an extract, transform, and load (ETL) module 310 transforms the image, as necessary to be used as input to the landmark engine 315. Additionally, the ETL module may extract relevant information (e.g., image dimensions, modality, etc.) to generate parameters for the landmark engine 315. The landmark engine 315 executes as described above with reference to FIG. 1A to identify a set of landmarks. Then, the machine learning model(s) 320 are executed on the set of landmark marks to produce a tagged image (i.e., an image with the appropriate body parts, etc. stored in metadata tags of the image. A data output module 325 is configured to communicate with a data repository 345 to store the tagged image. Additionally, a logging module 330 in the image processing system 335 records the tagged image and possibly other information used in processing the image (e.g., parameters to the landmark engine 315 and machine learning models 320). In this way, operation of the image processing system 335 can be verified and validated. Additionally, the logging module 330 may be used to debug the image processing system 335 if any erroneous tags or other data are detected.

Once the tagged image is stored in the data repository 345, a user 340 can access, retrieve, and use the tagged images. In some instances, the user 340 may provide feedback to the image processing system 335. In the example of FIG. 3, this feedback is provided to the image processing system 335; however, in other embodiments, the user 340 may provide the feedback to the data repository 345 which, in turn, relays the feedback to the image processing system 335. In some embodiments, the user may provide explicit feedback such as a rating, an accuracy measurement, etc. The feedback could also be to provide a ticket to correct a tag that was mis-tagged (because machine learning based systems are not 100% accurate in the beginning). In other embodiments, the feedback can be in the form of modification of the tags by the user 340. That is, the image processing system 335 may automatically detect any additions, deletions, or modifications to the metadata tags by the user 340. For example, the image processing system 335 may periodically review the contents of the data repository 345 to identify files with metadata tags modified by the user 340. The image processing system 335 may then use the image to retrain the machine learning models 320 to further increase their overall accuracy.

Figure 4:
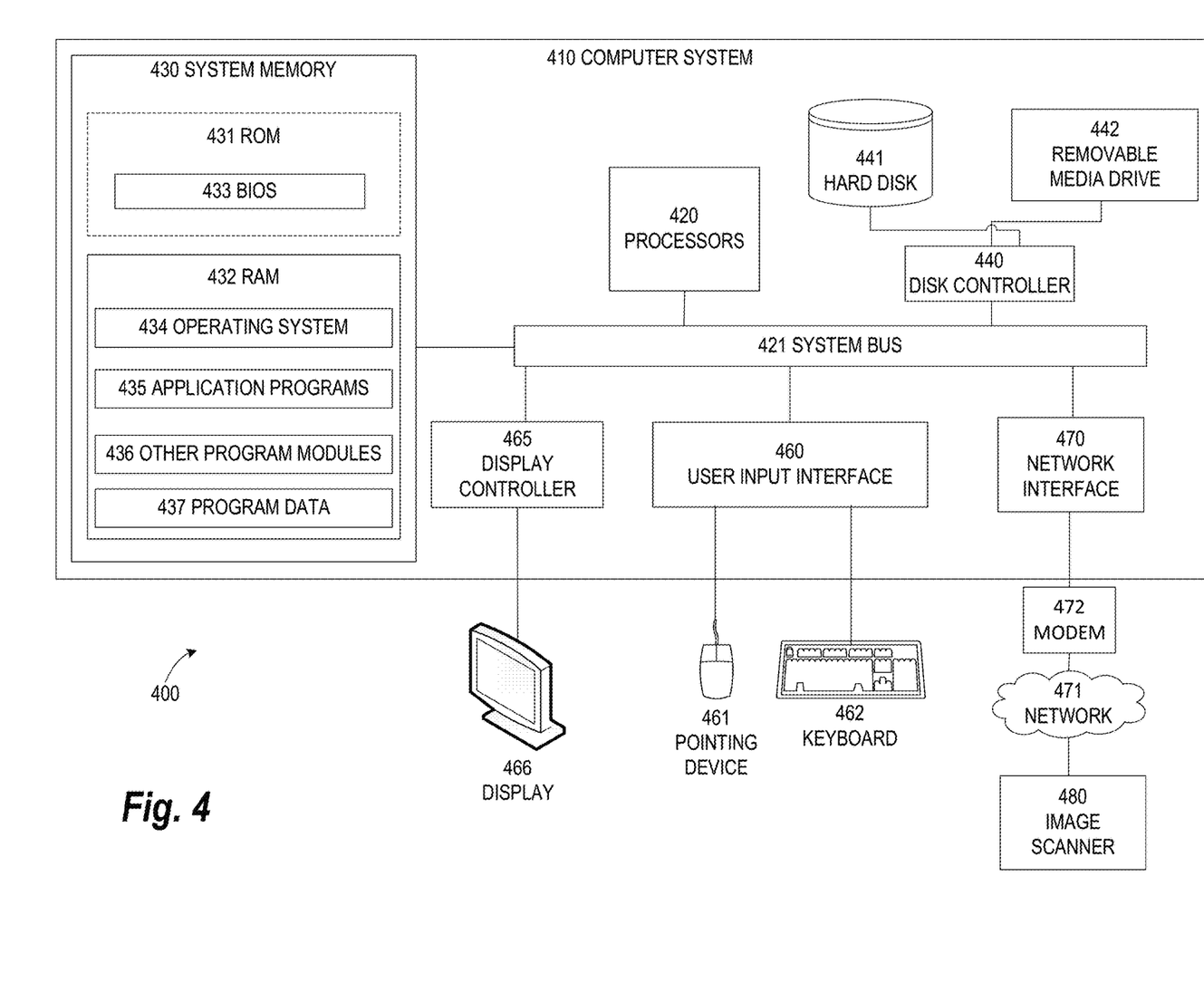
FIG. 4 illustrates an exemplary computing environment within which embodiments of the invention may be implemented.

FIG. 4 illustrates an exemplary computing environment 400 within which embodiments of the invention may be implemented. The computing environment 400 includes computer system 410, which is one example of a computing system upon which embodiments of the invention may be implemented. Computers and computing environments, such as computer system 410 and computing environment 400, are known to those of skill in the art and thus are described briefly herein.

As shown in FIG. 4, the computer system 410 may include a communication mechanism such as a bus 421 or other communication mechanism for communicating information within the computer system 410. The computer system 410 further includes one or more processors 420 coupled with the bus 421 for processing the information. The processors 420 may include one or more central processing units (CPUs), graphical processing units (GPUs), or any other processor known in the art.

The computer system 410 also includes a system memory 430 coupled to the bus 421 for storing information and instructions to be executed by processors 420. The system memory 430 may include computer readable storage media in the form of volatile and/or nonvolatile memory, such as read only memory (ROM) 431 and/or random access memory (RAM) 432. The system memory RAM 432 may include other dynamic storage device(s) (e.g., dynamic RAM, static RAM, and synchronous DRAM). The system memory ROM 431 may include other static storage device(s) (e.g., programmable ROM, erasable PROM, and electrically erasable PROM). In addition, the system memory 430 may be used for storing temporary variables or other intermediate information during the execution of instructions by the processors 420. A basic input/output system (BIOS) 433 contains the basic routines that help to transfer information between elements within computer system 410, such as during start-up, may be stored in ROM 431. RAM 432 may contain data and/or program modules that are immediately accessible to and/or presently being operated on by the processors 420. System memory 430 may additionally include, for example, operating system 434, application programs 435, other program modules 436 and program data 437. The application programs 435 may include, for example, the ETL module, the landmarking engine, the machine learning models, and the other components of the image processing system described above with reference to FIG. 3.

The computer system 410 also includes a disk controller 440 coupled to the bus 421 to control one or more storage devices for storing information and instructions, such as a hard disk 441 and a removable media drive 442 (e.g., floppy disk drive, compact disc drive, tape drive, and/or solid state drive). The storage devices may be added to the computer system 410 using an appropriate device interface (e.g., a small computer system interface (SCSI), integrated device electronics (IDE), Universal Serial Bus (USB), or FireWire).

The computer system 410 may also include a display controller 465 coupled to the bus 421 to control a display 466, such as a cathode ray tube (CRT) or liquid crystal display (LCD), for displaying information to a computer user. The computer system includes an input interface 460 and one or more input devices, such as a keyboard 462 and a pointing device 461, for interacting with a computer user and providing information to the processors 420. The pointing device 461, for example, may be a mouse, a trackball, or a pointing stick for communicating direction information and command selections to the processors 420 and for controlling cursor movement on the display 466. The display 466 may provide a touch screen interface which allows input to supplement or replace the communication of direction information and command selections by the pointing device 461.

The computer system 410 may perform a portion or all of the processing steps of embodiments of the invention in response to the processors 420 executing one or more sequences of one or more instructions contained in a memory, such as the system memory 430. Such instructions may be read into the system memory 430 from another computer readable medium, such as a hard disk 441 or a removable media drive 442. The hard disk 441 may contain one or more datastores and data files used by embodiments of the present invention. Datastore contents and data files may be encrypted to improve security. The processors 420 may also be employed in a multi-processing arrangement to execute the one or more sequences of instructions contained in system memory 430. In alternative embodiments, hard-wired circuitry may be used in place of or in combination with software instructions. Thus, embodiments are not limited to any specific combination of hardware circuitry and software.

As stated above, the computer system 410 may include at least one computer readable medium or memory for holding instructions programmed according to embodiments of the invention and for containing data structures, tables, records, or other data described herein. The term "computer readable medium" as used herein refers to any medium that participates in providing instructions to the processor 420 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 441 or removable media drive 442. Non-limiting examples of volatile media include dynamic memory, such as system memory 430. Non-limiting examples of transmission media include coaxial cables, copper wire, and fiber optics, including the wires that make up the bus 421. Transmission media may also take the form of acoustic or light waves, such as those generated during radio wave and infrared data communications.

The computing environment 400 may further include the computer system 410 operating in a networked environment using logical connections to one or more image scanners such as imaging device 480. The imaging device 480 may be a radiology scanner such as a magnetic resonance (MR) scanner, PET/MR, X-ray or a CT scanner. When used in a networking environment, computer system 410 may include modem 472 for establishing communications with the imaging device 480 or a remote computing system over a network 471, such as the Internet. Modem 472 may be connected to bus 421 via user network interface 470, or via another appropriate mechanism. It should be noted that, although the imaging device 480 is illustrated as being connected to the computer system 410 over the network 471 in the example presented in FIG. 4, in other embodiments of the present invention, the computer system 410 may be directly connected to the image scanner 480. For example, in one embodiment the computer system 410 and the image scanner 480 are co-located in the same room or in adjacent rooms, and the devices are connected using any transmission media generally known in the art.

Network 471 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 410 and other computers (e.g., remote computer 480). The network 471 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 471.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. The techniques described herein may generally be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A "graphical user interface" (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) the element is expressly recited using the phrase "means for."

We claim:

1. A computer-implemented method for automatically generating metadata tags for a medical image, the method comprising:
   receiving a medical image;
   automatically identifying a set of body landmarks in the medical image using one or more machine learning models;
   applying a set of rules to the set of body landmarks to identify anatomical objects present in the image;
   generating one or more metadata tags corresponding to the anatomical objects;
   storing the metadata tags in the medical image;
   transferring the medical image with the metadata tags to a data repository;
   receiving user feedback comprising a modification to one or more of the metadata tags associated with the medical image stored in the data repository; and
   updating the set of rules based on the received modification.

2. The method of claim 1, wherein the one or more machine learning models comprise a deep reinforcement learning model.

3. The method of claim 1, wherein each rule in the set of rules defines an upper bound landmark and a lower bound landmark for a corresponding anatomical object.

4. The method of claim 3, wherein each rule in the set of rules defines a left bound landmark and a right bound landmark for the corresponding anatomical object.

5. The method of claim 1, wherein the modification comprises a modification or deletion of one or more of the metadata tags.

6. The method of claim 1, wherein the modification comprises an addition of one or more new metadata tags.

7. The method of claim 1, wherein the medical image is acquired using a medical image scanner and the method is performed immediately following image reconstruction on a computer connected to the medical image scanner.

8. The method of claim 7, wherein the medical image scanner is a magnetic resonance imaging (MM) scanner.

9. A computer-implemented method for automatically generating metadata tags for a medical image, the method comprising:
receiving a medical image;
identifying a set of body landmarks in the medical image;
applying one or more machine learning models to the set of body landmarks to identify anatomical objects present in the image;
generating one or more metadata tags corresponding to the anatomical objects;
storing the metadata tags in the medical image;
transferring the medical image with the metadata tags to a data repository;
receiving user feedback comprising a modification to one or more of the metadata tags associated with the medical image stored in the data repository; and
retraining the one or more machine learning models based on the received modification.

10. The method of claim 9, wherein the one or more machine learning models comprise a random forest.

11. The method of claim 10, wherein the random forest is trained using a plurality of medical images labeled with an upper bound landmark, a lower bound landmark, and one or more labeled anatomical objects located between the upper bound landmark and the lower bound landmark.

12. The method of claim 11, wherein the plurality of medical images are further labeled with a left bound landmark and a right bound landmark, and the one or more labeled anatomical objects are located between the left bound landmark and the right bound landmark.

13. The method of claim 9, wherein the modification comprises a modification or deletion of one or more of the metadata tags.

14. The method of claim 9, wherein the modification comprises an addition of one or more new metadata tags.

15. The method of claim 9, wherein the medical image is acquired using a medical image scanner and the method is performed immediately following image reconstruction on a computer connected to the medical image scanner.

16. The method of claim 15, wherein the medical image scanner is a MM scanner.

17. A system for automatically generating metadata tags for a medical image, the method comprising:
a medical image scanner configured to acquire a medical image; and
an image processing system comprising one or more processors configured to
automatically identify a set of body landmarks in the medical image;
identify anatomical objects present in the image based on the set of body landmarks;
generate, using a program module configured to identify anatomical objects present in the image from the set of body landmarks, one or more metadata tags corresponding to the anatomical objects;
store the metadata tags in the medical image;
transfer the medical image with the metadata tags to a data repository;
receive user feedback comprising a modification to one or more of the metadata tags associated with the medical image stored in the data repository; and
adjust the program module based on the received modification.

18. The system of claim 17, wherein the medical image scanner is a MM scanner.

19. The system of claim 17, wherein:
the program module comprises a set of rules; and
the image processing system is configured to adjust the program module by updating the set of rules based on the received modification.

20. The system of claim 17, wherein:
the program module comprises one or more machine learning models; and
the image processing system is configured to adjust the program module by retraining the one or more machine learning models based on the received modification.

* * * * *